(12) United States Patent
Li et al.

(10) Patent No.: US 9,150,914 B2
(45) Date of Patent: Oct. 6, 2015

(54) METHODS AND COMPOSITIONS FOR AMPLIFICATION AND SEQUENCING OF DIFFICULT DNA TEMPLATES

(71) Applicant: GENEWIZ INC., SUZHOU, Suzhou, Jiangsu (CN)

(72) Inventors: Shihong Li, Berkeley Heights, NJ (US); Narisra Jongkam, Highland Park, NJ (US); Shifang Zhang, New York, NY (US); Conrad Leung, Edison, NJ (US)

(73) Assignee: Genewiz Inc., Suzhou, Suzhou, Jiangsu (CN)

( * ) Notice: Subject to any disclaimer, the term of this patent is extended or adjusted under 35 U.S.C. 154(b) by 127 days.

(21) Appl. No.: 13/852,711

(22) Filed: Mar. 28, 2013

(65) Prior Publication Data

US 2013/0316352 A1    Nov. 28, 2013

Related U.S. Application Data

(60) Provisional application No. 61/617,245, filed on Mar. 29, 2012.

(51) Int. Cl.
*C12Q 1/68* (2006.01)
*C07H 15/00* (2006.01)

(52) U.S. Cl.
CPC ........ *C12Q 1/6869* (2013.01); *C12Q 2525/117* (2013.01); *C12Q 2531/125* (2013.01)

(58) Field of Classification Search
CPC ........... C12Q 1/6869; C12Q 2525/117; C12Q 2531/125
USPC ........................................... 435/6.12; 536/4.1
See application file for complete search history.

(56) References Cited

PUBLICATIONS

"ABI Prism dGTP BigDye™ Terminator v3.0 Ready Reaction Cycle Sequencing Kit", Applied Biosystems (2002), https://tools.invitrogen.com/content/sfs/manuals/cms_041496.pdf accessed Aug. 5, 2013.
Dierick, H., et al., "Incorporation of DITP or 7-deaza dGTP during PCR improves sequencing of the product", Nucleic Acids Research, 21(18):4427-4428 (1993).
Keith, J. M., et al., "Unlocking hidden genomic sequence", Nucleic Acids Research, 32(3):1-9 (2004).
Suspéne, R., et al., "Inversing the natural hydrogen bonding rule to selectivity amplify GC-rich ADAR-edited RNAs", Nucleic Acids Research, 36(12): 1-10 (2008).

*Primary Examiner* — Jezia Riley
(74) *Attorney, Agent, or Firm* — Scully, Scott, Murphy & Presser P.C.

(57) ABSTRACT

This disclosure provides methods and compositions for amplification and sequencing of DNA templates, comprising at least two of: 2'-deoxyinosine-5' triphosphate, 5-propynyl-2'-deoxycytidine-5'-triphosphate, and 8-oxo-2'-deoxyguanosine-5'-triphosphate. Incorporation of these promoting nucleotides into amplification and sequencing reactions improves the amplification and sequencing of difficult-to-sequence DNA regions such as a GC rich regions or GT rich regions; repetitive sequences, including dinucleotide, trinucleotide, direct, inverted, Alu, poly A or poly T repeats; and hairpin or other secondary structures.

7 Claims, 18 Drawing Sheets
(18 of 18 Drawing Sheet(s) Filed in Color)

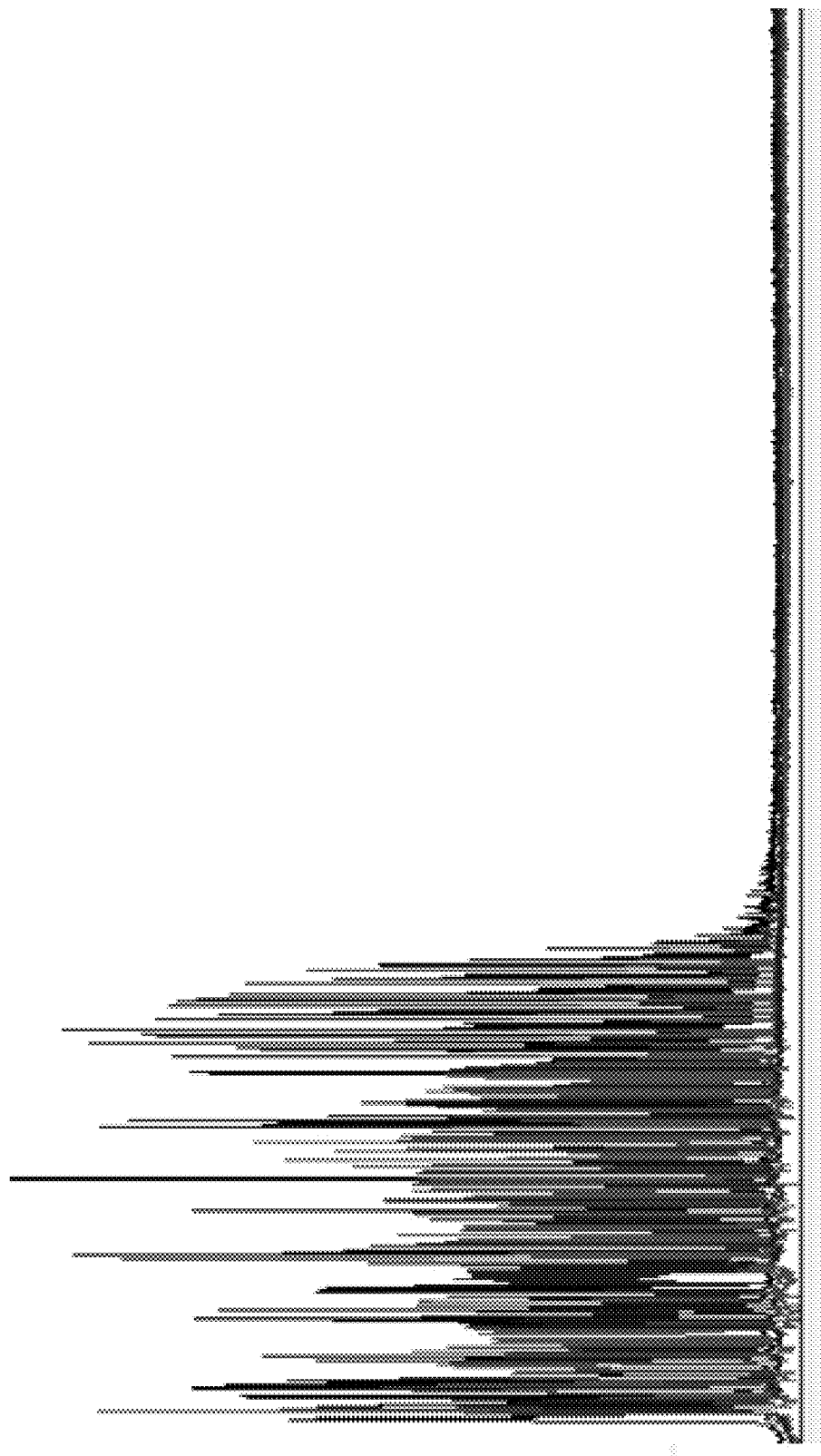

SEQUENCE LISTING

```
<160> NUMBER OF SEQ ID NOS: 11

<210> SEQ ID NO 1
<211> LENGTH: 106
<212> TYPE: DNA
<213> ORGANISM: Artificial Sequence
<220> FEATURE:
<223> OTHER INFORMATION: Synthetic Oligonucleotide

<400> SEQUENCE: 1
acggccccgg accatatttta ttgcatgact gctgcagcag tcatgcaata aatatggtcc    60
ggggccgggg gatccgtggt ctcatacaga acttataaga ttccca                   106

<210> SEQ ID NO 2
<211> LENGTH: 25
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (24)..(24)
<223> OTHER INFORMATION: n is a, c, g, or t

<400> SEQUENCE: 2
ggccccggac catatttatt gcang                                          25

<210> SEQ ID NO 3
<211> LENGTH: 64
<212> TYPE: DNA
<213> ORGANISM: Artificial Sequence
<220> FEATURE:
<223> OTHER INFORMATION: Synthetic Oligonucleotide

<400> SEQUENCE: 3
ggccccggac catatttatt gcatgactgc tgcagcagtc atgcaataaa tatggtccgg    60
ggcc                                                                 64

<210> SEQ ID NO 4
<211> LENGTH: 66
<212> TYPE: DNA
<213> ORGANISM: Artificial Sequence
<220> FEATURE:
<223> OTHER INFORMATION: Synthetic Oligonucleotide

<400> SEQUENCE: 4
acggccccgg accatatttta ttgcatgact gctgcagcag rcatgcaata gatatggtcc   60
ggggcc                                                               66

<210> SEQ ID NO 5
<211> LENGTH: 65
<212> TYPE: DNA
<213> ORGANISM: Artificial Sequence
<220> FEATURE:
<223> OTHER INFORMATION: Synthetic Oligonucleotide
```

-continued

```
<400> SEQUENCE: 5
acggccccgg accatatttg tgcatgacag ctgcagcagt catgcactaa atatggtccg      60
gggcc                                                                  65

<210> SEQ ID NO 6
<211> LENGTH: 64
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (24)..(25)
<223> OTHER INFORMATION: n is a, c, g, or t

<400> SEQUENCE: 6
acggccccgg accatatttg tgtnnactgc tgcagcagrc atgcaaggag atgggcccgg      60
ggcc                                                                   64

<210> SEQ ID NO 7
<211> LENGTH: 66
<212> TYPE: DNA
<213> ORGANISM: Artificial Sequence
<220> FEATURE:
<223> OTHER INFORMATION: Synthetic Oligonucleotide

<400> SEQUENCE: 7
cggccccgga ccatatttat tgcatgactg ctgcagcagt catgcaataa atatggtccg      60
gggccg                                                                 66

<210> SEQ ID NO 8
<211> LENGTH: 66
<212> TYPE: DNA
<213> ORGANISM: Artificial Sequence
<220> FEATURE:
<223> OTHER INFORMATION: Synthetic Oligonucleotide

<400> SEQUENCE: 8
cggccccgga ccatatttat tgcatcactg ctgcagcagt catgcaataa atatggtccg      60
gggccg                                                                 66

<210> SEQ ID NO 9
<211> LENGTH: 66
<212> TYPE: DNA
<213> ORGANISM: Artificial Sequence
<220> FEATURE:
<223> OTHER INFORMATION: Synthetic Oligonucleotide

<400> SEQUENCE: 9
ggccccggac catatttatt gcatgactgc tgcagcagrc atgcaataaa tatggtccgg      60
ggccgg                                                                 66

<210> SEQ ID NO 10
<211> LENGTH: 126
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (99)..(101)
<223> OTHER INFORMATION: n is a, c, g, or t
<220> FEATURE:
```

```
<221> NAME/KEY: misc_feature
<222> LOCATION: (103)..(105)
<223> OTHER INFORMATION: n is a, c, g, or t
<220> FEATURE:
<221> NAME/KEY: misc_feature
<222> LOCATION: (107)..(107)
<223> OTHER INFORMATION: n is a, c, g, or t
<220> FEATURE:
<221> NAME/KEY: misc_feature
<222> LOCATION: (112)..(119)
<223> OTHER INFORMATION: n is a, c, g, or t
<220> FEATURE:
<221> NAME/KEY: misc_feature
<222> LOCATION: (122)..(126)
<223> OTHER INFORMATION: n is a, c, g, or t

<400> SEQUENCE: 10
aggtggtgtg ggtgtggtgt gtgggtgtgg tgtgtgggtg tggtgtgggt gtgtgggtgt      60
ggtgtgtgtg ggtgtgtggg tgtgggtgtg gtgtgtggnn ntnnngnccc cnnnnnnnnc    120 cnnnnn                                                                126

<210> SEQ ID NO 11
<211> LENGTH: 130
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (127)..(130)
<223> OTHER INFORMATION: n is a, c, g, or t

<400> SEQUENCE: 11
gtgaggtggt gtgggtgtgg tgtgtgggtg tggtgtgtgg gtgtggtgtg ggtgtgtggg      60
tgtgtggtgt gtgggtgtgt gggtgtgggt gtggtgtgtg ggtgtggtgt cccccccccc    120 ccccccnnnn                                                            130
```

METHODS AND COMPOSITIONS FOR AMPLIFICATION AND SEQUENCING OF DIFFICULT DNA TEMPLATES

CROSS-REFERENCE TO RELATED APPLICATIONS

This application claims priority to U.S. provisional application No. 61/617,245, filed Mar. 29, 2012, which is incorporated herein in its entirety.

INCORPORATION BY REFERENCE OF SEQUENCE LISTING

The Sequence Listing in the ASCII text file, named as 29721_ST25.txt of 4 KB, created on Jul. 31, 2013, and submitted to the United States Patent and Trademark Office via EFS-Web, is incorporated herein by reference.

BACKGROUND OF THE DISCLOSURE

The holy grail of life is written in four letters in one's genome. The ability to read and understand the 4-lettered text holds the key to understanding of life in general and all its quirky details. Two methods emerged in the 1970s to decipher the exact sequence of the four nucleotides; Guanine (G), Adenine (A), Thymidine (T) and Cytosine (C) in a sequence of DNA. The chemical sequencing method, developed by Gilbert and Maxam, is based on chemical modification of DNA and subsequent cleavage at specific sites (Maxam A M, Proc. Natl. Acad. Sci. U.S.A. 74 (2): 560-4 (1977)). The chain termination method, developed by Sanger, makes use of dideoxynucleotide triphosphates (Sanger F, Proc Natl Acad Sci USA. 74(12): 5463-5467 (1977)). Owing to its relative ease and reliability, Sanger sequencing has become the method of choice.

The Sanger reaction requires a single stranded DNA template, a primer, a DNA polymerase, four normal deoxynucleotide triphosphates (dNTPs) to extend the primer, and four dideoxynucleotide triphosphates (ddNTPs) to terminate DNA strand elongation, resulting in DNA fragments of varying length. In the classic Sanger reaction, ddNTPs are radiolabeled and final DNA fragments are separated by electrophoresis in polyacrylamide gel and visualized by autoradiography, allowing direct reading of the DNA sequence from the autoradiograph. Tagging the primer, and particularly tagging the ddNTPs, with fluorescent dye set the stage for automated DNA sequencing (Smith L M, et al., Nucl. Acids Res. 13(7): 2399-2412 (1985); Smith L M, et al., Nature 321:674-9 (1986)).

Modifications to basic Sanger sequencing include methods and products for combined amplification and sequencing reactions, such as the BigDye series by Applied Biosystems Inc. (ABI). The protocol for use of BigDye and similar amplification and sequencing techniques is as follows. Double stranded DNAs are denatured by heat to single stranded templates, annealed to a proper primer, and Taq DNA polymerase then extends the template with dNTPs and terminates elongation with ddNTPs. The ddNTPs are base-labeled with energy-transfer fluorescent dyes, which can be excited at one wave length and emits light of different wavelength. By repeated thermal denaturing and DNA synthesis, a pool of DNA fragments, each ending with a single fluorescently labeled ddNTP, is generated. The fragments are separated by capillary electrophoresis, visualized under laser as electronic chromatograms. The DNA sequence can then be read automatically using a number of software packages.

Sanger sequencing enabled sequencing of the first human genome. However, many challenges remain to be tackled, such as template-related sequencing difficulties. For example, DNA secondary structure, repetitive sequences, long stretches of homopolymers, circular DNA, and tightly-adhered sequences represent some of the many sequence-related obstacles faced in Sanger sequencing methods. There is a great need to overcome these and other template-related obstacles to improve sequencing methods.

BRIEF SUMMARY OF THE DISCLOSURE

This disclosure provides compositions and methods for improved amplification and sequencing of DNA. The inventors have discovered that the addition of specific modified nucleotides to amplification and sequencing reactions improves the amplification and sequencing of problematic DNA sequences, such as DNA sequences that have repetitive sequences, homopolymer stretches, and/or secondary structures such as hairpin loops.

As a first embodiment, this disclosure provides improved compositions for amplification and sequencing of DNA templates, where the compositions include at least two of three nucleotides selected from 2'-deoxyinosine-5' triphosphate ("dITP"), 5-propynyl-2'-deoxycytidine-5'-triphosphate ("5-propynyl-dCTP"), and 8-oxo-2'-deoxyguanosine-5'-triphosphate ("8-oxo-dGTP").

The composition can include dITP and 5-propynyl-dCTP, or dITP and 8-oxo-dGTP, or 5-propynyl-dCTP and 8-oxo-dGTP, or all three of dITP, 8-oxo-dGTP, and 5-propynyl-dCTP. Any one of dITP, 5-propynyl-dCTP, and/or 8-oxo-dGTP can be present in the composition in the range of 1 µM to 5 mM, preferably 5 µM to 400 µM. Preferred ratios of dITP to 8-oxo-dGTP in the composition, or dITP to 5-propynyl-dCTP in the composition, are between 100:1 to 2:1, preferably between 20:1 to 2:1.

The compositions disclosed herein promote amplification and/or sequencing of DNA which may be difficult to sequence using standard reagents and techniques, including circular or linear DNA, particularly circular or linear DNA containing one or more of: a GC-rich region, a repetitive sequence, or a hairpin secondary structure. In a preferred embodiment, the compositions of the invention promote or improve sequencing of circular DNA containing a GC-rich region, a repetitive sequence, or a hairpin secondary structure.

A composition including any two or all three of dITP, 8-oxo-dGTP, and 5-propynyl-dCTP can further include: a mixture of nucleotides dATP, dCTP, and dUTP; a mixture of fluorescently labeled nucleotides ddATP, ddCTP, ddGTP and ddTTP; at least one thermostable DNA polymerase; a thermostable pyrophosphatase; Tris buffer, pH 8.5-9.5; and magnesium salt. Such compositions are contemplated for use, in direct DNA sequencing. In these compositions, dATP, dCTP, and dUTP can each be present in the composition in the range of 10 µM to 250 µM, while the fluorescently labeled ddNTPs can each be present in the composition in the range of 1 nM to 1 µM. One of the at least one thermostable DNA polymerases can be a Taq polymerase, such as Taq polymerase that has a low level 5'-3' nuclease activity and can readily incorporate fluorescently labeled dideoxynucleotides. Such a Taq polymerase can be present in the composition in the range of 0.5-1 unit/µl. The pyrophosphatase can be, for example, recombinant Thermus thermophilus (rTth) pyrophosphate in the range of 0.5-2 unit/µl, and the magnesium salt can be present in the composition in the range of 0.5-10 mM.

In another embodiment of the invention, a composition including any two or all three of dITP, 8-oxo-dGTP, and 5-propynyl-dCTP can further include: a mixture of nucleotides dATP, dCTP, dGTP and dTTP; a random primer; a DNA polymerase; a compatible buffer, such as Tris buffer, pH 7-8; and salts, such as magnesium salt and ammonia sulfate salts. Such compositions are contemplated for use, for example, for rolling circle DNA amplification, or for rolling circle DNA amplification followed by DNA cycle sequencing. In a composition of this nature, dATP, dCTP, dGTP and dTTP can each be present in the range of 10 µM to 250 µM. The DNA polymerase can be, for example, phage (Phi) 29 DNA polymerase, preferably in the range of 0.1 unit/µl to 5 units/µl. The magnesium salt can be present in the range of 0.5-10 mM, and the ammonia sulfate salts can be present in the range of 0.5-10 mM.

Further disclosed herein are methods for amplifying a DNA template, which include the steps of: providing a DNA template and an exonuclease-resistant random hexamer primer; denaturing the DNA template; annealing the primer to the DNA template; and incubating the template and the primer with a composition including any two or all three of dITP, 8-oxo-dGTP, and 5-propynyl-dCTP, and which can further include the composition described above for rolling circle amplification, for a time sufficient for the DNA template to be amplified. These methods are particularly effective for the amplification of circular DNA templates, even more particularly for circular DNA templates that have at least one region of GC rich sequence, repetitive sequence, or hairpin secondary structure. For amplification of circular DNA, the template is preferably provided in an amount of 1 ng to 500 ng, and the primer is preferably provided in an amount of 1 µM to 100 µM. In addition, according to these methods, the template and primer can be incubated together at 25-35° C., preferably 28-32° C., for 1-18 hours.

This disclosure further provides methods for direct sequencing of a DNA template that include: providing a DNA template; denaturing the DNA template; providing a primer for the DNA template; annealing the primer to the DNA template; incubating the template and the primer with a composition that includes any two or all three of dITP, 8-oxo-dGTP, and 5-propynyl-dCTP, and which can further include the composition described above for direct cycle sequencing; performing DNA replication of the template; purifying the replicated DNA to remove free nucleotides; and obtaining the sequence of the template. These methods are particularly effective for direct sequencing of DNA templates that have at least one region of GC rich sequence, repetitive sequence, or a hairpin secondary structure.

In these methods, the DNA template is preferably provided in the range of 25 ng to 500 ng, while the primer is preferably provided in the range of 0.1 µM to 10 µM. The DNA replication step can be performed for 20-40 cycles where each cycle can include, for example, the following sequence of steps: 10-14 seconds at 94-97° C., 4-8 seconds at 49-51° C. and 60-180 seconds at 59-61° C. The sequence of the DNA template can be obtained by capillary electrophoresis of the replicated DNA. For direct cycle sequencing of circular DNA, the circular DNA template can be amplified using Phi29 DNA polymerase.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 5A-5E. Sequence chromatogram of a DNA template with a 334 bp stretch of GT repeats, followed by a 23 bp stretch of poly C repeats, sequenced after RCA amplification with standard nucleotides and (A) dITP; (B) 5-propynyl-dCTP; (C) dITP and 5-propynyl-dCTP; (D) dITP and 8-oxo-dGTP or (E) dITP, 5-propynyl-dCTP, and 8-oxo-dGTP.

DETAILED DESCRIPTION OF THE DISCLOSURE

Figure 1:
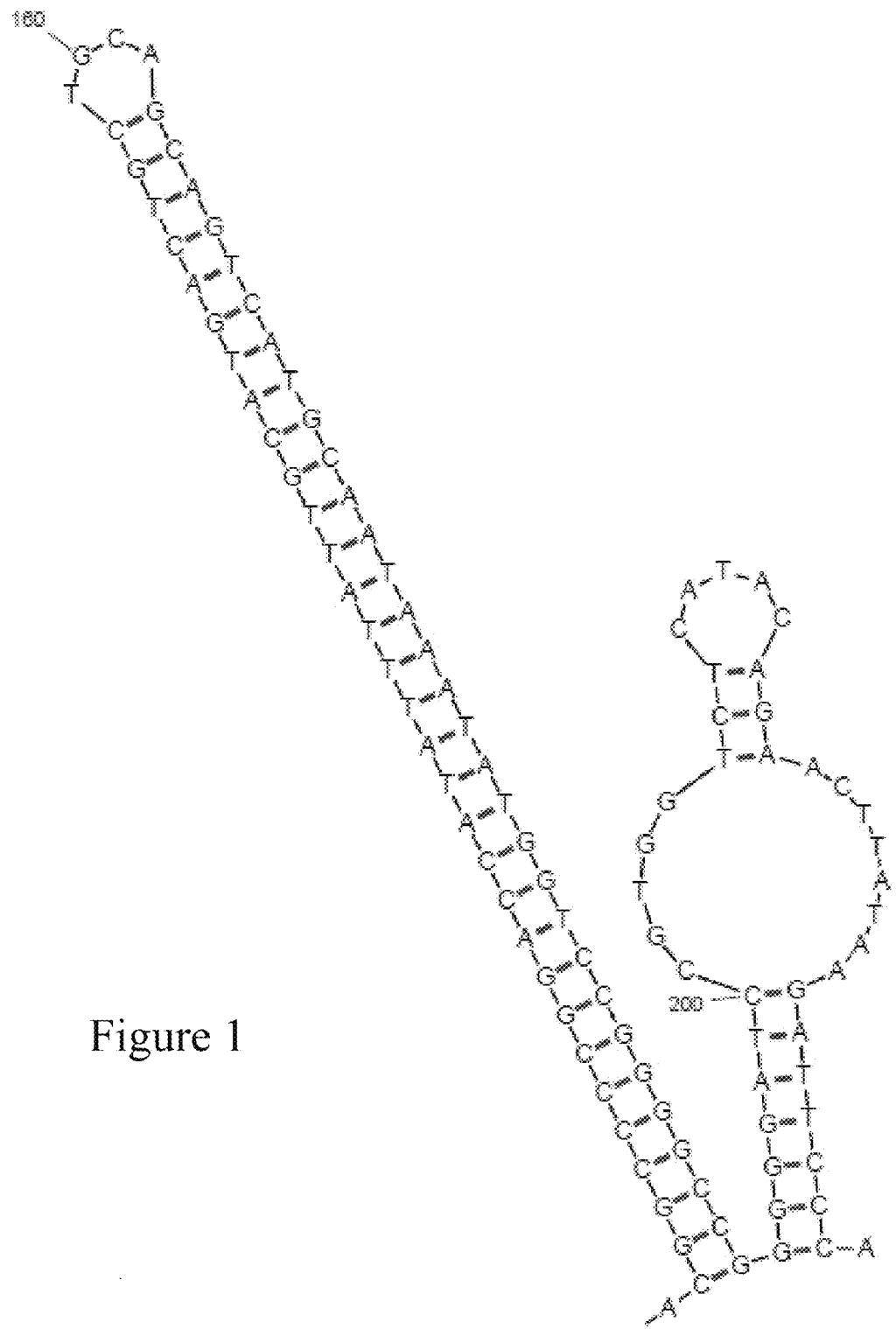
FIG. 1. DNA template with a 33 base pair hairpin (nucleotide sequence, SEQ ID NO: 1).

The present invention provides compositions and methods to promote the amplification and sequencing of DNA, particularly DNA with secondary structures, repetitive sequences, and other structure or sequence-related barriers that present obstacles to amplification and sequencing using standard techniques. The inventors have determined that compositions for amplification and/or sequencing that include two or three of the specific modified dNTPs according to the invention provide improved lengths of continuous DNA amplification, and improved read-through during sequencing.

The inventors have found that amplification and sequencing compositions that contain combinations of two or all three of 2'-deoxyinosine-5' triphosphate ("dITP"), 5-propynyl-2'-deoxycytidine-5'-triphosphate ("5-propynyl-dCTP") and 8-oxo-2'-deoxyguanosine-5'-triphosphate ("8-oxo-dGTP") (referred to herein as "promoting nucleotides" or "promoting dNTPs") provide unexpectedly improved results over other compositions for amplification and sequencing of difficult DNA templates. The combination compositions disclosed herein even show improved results compared to amplification or sequencing compositions that contain only one of the amplification-promoting dNTPs disclosed herein.

Certain DNA sequences are difficult or problematic to amplify and sequence using standard Sanger sequencing protocols and reagents. During the amplification steps by DNA polymerase, the enzyme typically stalls and cannot "read through" these sequences, leading to DNA replicate copies that are truncated before or within the problematic region. A "difficult" DNA sequence can contain one or more of the following: a GC rich region or GT rich region; repetitive sequence, including dinucleotide, trinucleotide, direct, inverted, Alu, poly A or poly T repeats; hairpin structures, such as with two or more inverted repeats separated by 3 or more nucleotides. DNA can contain one, two, or three of more of such hard-to-amplify regions. For example, a DNA template can contain trinucleotide repeats followed by homopolymers.

The term "GC-rich region" refers to a segment of a nucleic acid wherein at least 55%, 65%, 75%, or 85% or more of the bases comprise a guanine or a cytosine nucleotide. Similarly, the term "GT-rich region" refers to a region of a nucleic acid wherein at least 55%, 65%, 75%, or 85% or more of the bases comprise a guanine or a thymine nucleotide.

The term "repetitive sequence" refers to a segment of DNA containing a sequence of nucleotides that is repeated for at least 5, 10, 15, 20, 30, 40, 50, 60, 80, or 100 or more nucleotide bases. Repetitive sequences can include single nucleotide repeats (homopolymer stretches, e.g., poly A or poly T tails), di-nucleotide repeats (e.g., ATAT or AGAG), trinucleotide repeats, tetranucleotide repeats, telomeric repetitive elements and the like. Repetitive sequences also include, but not limited to, ALU, LINE (long interspersed genetic elements, which are non-coding), SINE (short interspersed genetic elements, which also are non-coding), and certain transposons such as L and P element sequences. ALU elements are a type of SINE element, roughly 300 base pairs in length, with a typical structure of 5'Part A—A5TACA6—Part B—PolyA Tail-3', where Part A and Part B are similar peptide sequences, but of opposite direction.

Secondary structures in a single-stranded nucleic acid, such as ribosomal RNA or denatured DNA, arise from the intramolecular formation of hydrogen bonds between complementary nucleotide sequences within the single-stranded nucleic acid itself. This residual secondary structure can sterically inhibit, or even block, enzyme activity and hybrid formation between a nucleotide being added during extension of a DNA strand being synthesized, and its complementary sequence in the DNA template. Secondary structures include, but are not limited to, hairpins, pseudoknots, and tetraloops. Hairpins, also called stem-loop structures, are self-complementary regions where the single stranded sequence binds back on itself to form a double helix, typically with a small loop of unpaired bases between the paired regions (see, for example, FIG. 1). Tetraloops are a type of multi-hairpin sequence that form a "cloverleaf", such as in tRNA structures. Pseudoknots are a type of hairpin containing at least two stem-loop structures in which half of one stem is intercalated between the two halves of another stem.

According to the present invention, addition of the promoting nucleotides disclosed herein enables sequencing of linear and circular DNA, and various types of difficult templates with secondary structures and combinations of secondary structures and repetitive elements. The combination of 2 to 3 of the following nucleotides, particularly, helps overcome enzyme stalls and DNA replication difficulties associated with circular or linear DNA, particularly circular or linear DNA containing one or more of: a GC rich or GT rich region, a repetitive sequence, or a hairpin secondary structure.

Circular DNA is any form of DNA that forms a complete closed circle, in contrast to a linear DNA molecule which does not. Circular DNA can be double-stranded or single stranded. Examples of circular DNA include plasmids, episomes, and bacterial and viral genomes. A few picagram of circular DNA can expand to several hundred of microgram after a few hours of rolling circle amplification.

2'-deoxyinosine-5' triphosphate (dITP) is a common nucleotide widely available from multiple venders. 5-propynyl-2'-deoxycytidine-5'-triphosphate (5-propynyl-dCTP) and 8-oxo-2'-deoxyguanosine-5'-triphosphate (8-oxo-dGTP) can be purchased from TriLink Biotechnologies. Each of these nucleotides can be used in the compositions disclosed herein in the range of range of 1 µM to 5 mM, and preferably 5 µM to 400 µM.

The compositions disclosed herein can include dITP and 5-propynyl-dCTP, or dITP and 8-oxo-dGTP, or 5-propynyl-dCTP and 8-oxo-dGTP, or all three of dITP, 8-oxo-dGTP, and 5-propynyl-dCTP. Any one of dITP, 5-propynyl-dCTP, and/or 8-oxo-dGTP can be present in the composition in the range of 5 µM to 5 mM, preferably 5 µM to 400 µM. Preferred ratios of dITP to 8-oxo-dGTP in the composition, or dITP to 5-propynyl-dCTP in the composition, are between 100:1 to 2:1, preferably between 20:1 to 2:1.

Deoxyribonucleotide triphosphates (dNTPs) are utilized in amplification and sequencing reactions. Standard dNTPs are dATP, dGTP, dCTP, and dTTP. In some sequencing compositions such as BigDye sequencing kits (Applied Biosystems Inc.), dTTP is replaced with dUTP. The promoting dNTPs provided herein can be used in addition to, or as a substitute for, standard dNTPs. For example, dITP and 8-oxo-dGTP can be used as a substitute for dGTP, and 5-propynyl-dCTP can substitute for dCTP.

During DNA amplification, promoting dNTPs are incorporated into the DNA replicate strand by DNA polymerase. Without being bound, it is believed that the side chains of dITP, 5-propynyl-dCTP, and 8-oxo-dGTP make these nucleotides "bulkier" than a standard dNTP, and the resulting replicate strands anneal less tightly to both the template molecule sequence, to other replicate strands, and to itself. Accordingly, any secondary structure of the DNA annealing to itself, or any annealing of the replicate DNA to another strand, is weakened and therefore easier to separate, amplify, and "read" by subsequent sequencing methods.

dATP, dCTP, dITP and dUTP are widely available from multiple venders. Fluorescently-labeled ddATP, ddCTP, ddGTP, and ddTTP can be purchased, for example, as components of BigDye from ABI, or as components of the DYEnamic ET terminator cycle sequencing kit from GE Healthcare Life Science. Alternatively, the fluorescently labeled ddNTPs can be synthesized as described in U.S. Pat. No. 5,945,526 or U.S. Pat. No. 6,967,250.

Any combination of two or three of the promoting nucleotides can be added to any DNA replication or amplification reactions involving any DNA polymerases, including mesophilic DNA polymerases such as Klenow, DNA polymerase I, T7 polymerase or derivatives, T5 DNA polymerase, Phage (Phi)29 DNA polymerase, or RB69 DNA polymerase; or for amplification using thermostable DNA polymerases such as Bst (*Bacillus stearothermophilus*) DNA polymerase, Taq (*Thermus aquaticus*) DNA polymerase and modified Taq polymerases such as AmpliTaq (Invitrogen), Tth (*Thermus thermophilus*) DNA polymerase, Tma DNA polymerase, Pfu (*Pyrococcus furiosus*) DNA polymerase, Phusion DNA polymerase, Vent DNA polymerase, etc.

The promoting nucleotides can also be added to any RNA reverse transcription reaction involving any reverse transcriptase, including AMV Reverse transcriptase, M-MuLV reverse transcriptase, etc. Thermostable pyrophosphate serves to remove the pyrophosphates (PPi) generated and accumulated in DNA synthesis reaction, and is commercially available, e.g., from New England Biolab, (M0296).

The compositions and methods of the present invention can be utilized in all types of sequencing, including, for example, pyrosequencing, semiconductor sequencing, Illumina sequencing, and SMRT sequencing. The same approach can be applied to amplification of difficult templates, including PCR amplification, isothermal amplification and rolling—circle amplification. The same approach can also be applied to hybridization techniques for identification of DNA sequences, including Southern, Northern, and array hybridization and target enrichment methods.

The present invention provides methods and compositions for sequencing DNA containing strong secondary structure and/or repetitive sequence, either directly, or after initial amplification.

In one embodiment, methods and compositions are presented for direct DNA sequencing (a combined DNA strand extension/amplification and sequencing reaction that differs from traditional PCR in part in the use of a single primer that allows amplification to proceed in only one direction, where each amplified strand is terminated by incorporation of a ddNTP)

An exemplary composition includes any two or all three of dITP, 8-oxo-dGTP, and 5-propynyl-dCTP, and further includes: a mixture of nucleotides dATP, dCTP, and dUTP; a mixture of fluorescently labeled nucleotides ddATP, ddCTP, ddGTP and ddTTP; at least one thermostable DNA polymerase; a thermostable pyrophosphatase; Tris buffer, pH 8.5-9.5; and magnesium salt. dATP, dCTP, and dUTP can each be present in the composition in the range of 10 µM to 250 µM, while the fluorescently labeled nucleotides can each be present in the composition in the range of 1 nM to 1 µM. One of the at least one thermostable DNA polymerases can be a Taq polymerase, such as a thermally activated Taq polymerase. Such a Taq polymerase can be present in the composition in the range of 0.5-1 unit/µl. The pyrophosphatase can be, for example, recombinant *Thermus thermophilus* (rTth) pyrophosphate in the range of 0.5-2 unit/µl, and the magnesium salt can be present in the composition in the range of 0.5-10 mM.

For example, any combination of the promoting nucleotides can be added to a cycle sequencing reaction catalyzed by a group A DNA polymerase, such as Taq polymerase, preferably AmpliTaq FS (Applied Bioscience/Roche BioScience). Taq can be substituted with any thermostable DNA polymerase that has low level 5'-3' nuclease activity and can readily incorporate dideoxynucleotides. To reduce or eliminate 5'-3' nuclease activity from Taq polymerase, one can delete up to 191 residues of the N-terminal domain or introduce a G46D mutation in the exo-nuclease domain. To accommodate nucleotide analogues including ddNTPs and the promoting nucleotide combo, one can introduce the F667Y mutation in the active site of the enzyme (Li, Y. et al., *EMBO Journal*, 17:7514-7525 (1998)). Other thermostable enzymes can be modified to serve such purposes, by introducing similar mutations in the corresponding active site domains (See, e.g., U.S. Patent Publication No. 2003/0228589).

For direct sequencing, the composition includes the promoting nucleotides mixed with a mixture of dATP, dCTP, dITP and dUTP, each of which is in the range of 10 µM to 250 µM; a mixture of fluorescently-labeled ddATP, ddCTP, ddGTP, and ddTTP each in the range of 1 nM to 1 µM; thermostable polymerase such as AmpliTaq FS in the range of 0.5 unit/µl to 1 unit/µl; and thermostable pyrophosphatase such as rTth pyrophosphatase in the range of 0.5-2 unit/µl. These components are prepared with a suitable buffer and salts, such as Tris buffer, pH 8.5-9, and magnesium salt in the range of 0.5-10 mM. Circular DNA templates can be replicated using phage 29 DNA polymerase as the thermostable polymerase prior to sequencing.

In direct sequencing methods, the above composition is incubated with the DNA template and primer, the DNA template being preferably provided in the range of 2.5 ng to 500 ng, while the primer is preferably provided in the range of 0.1 µM to 10 µM. DNA replication of the template is performed during the incubation, which includes multiple cycles of repeated steps of (a) annealing of the primer to the template; (b) extension of the replicate DNA strand by DNA polymerase; and (c) termination of the extending DNA strand. The DNA replication step can be performed for 20-40 cycles where each cycle can include, for example, the following sequence of steps: 10-14 seconds at 94-97° C., 4-8 seconds at 49-51° C. and 60-180 seconds at 59-61° C. The DNA replicate sequences are randomly terminated at various positions with incorporation of ddNTP, resulting in accumulation of product with various lengths.

After cycling, the reaction products can be precipitated using standard procedures, washed and re-suspended in, e.g. formamide loading buffer. The replicated DNA can be purified to remove free nucleotides. The purified replicated DNA can then be loaded onto a sequencing instrument, such as an ABI 3730 (Applied Biosystems) or a MagaBACE 1000 (GE Healthcare Bioscience). The purified replicated strands can be separated, for example, by capillary electrophoresis. The sequence of the DNA template can be obtained by standard techniques, such as capillary electrophoresis of the replicated DNA. The sequence can then be deciphered using standard software. These methods are particularly effective for direct sequencing of DNA templates that have at least one region of GC rich sequence, repetitive sequence, or a hairpin secondary structure.

The above-described methods and compositions using the promoting nucleotides for direct sequencing of DNA segments are effective for sequencing many types of DNA; however, these methods and compositions are particularly effective for sequencing of difficult DNA templates containing hairpin or other secondary structures.

In another embodiment, the promoting nucleotides of the invention are used in compositions and methods for rolling circle amplification (RCA). Rolling circle amplification provides amplification of a DNA template by the following mechanism. A DNA primer is annealed to a circular DNA template. DNA polymerase then extends the primer continuously around the circular DNA template, generating a long DNA product that consists of many repeated copies of the circle. By the end of the reaction, the polymerase generates many thousands of copies of the circular template.

Any combination of the promoting nucleotides can be added to rolling circle amplification catalyzed by DNA polymerases with strand displacement activity (that is, a DNA polymerase having the ability to displace downstream DNA encountered during synthesis). Examples of strand displacing DNA polymerases include, but are not limited to, *Bacillus stearothermophilus* (Bst) DNA Polymerase I, Klenow fragment, and Phi29 DNA polymerase. In one example of these compositions and methods, the above mentioned promoting nucleotides are combined with a circular template annealed to exonuclease-resistant random hexamer; a mixture of dATP, dCTP, dGTP and dTTP, each of which is in the range of 10 µM to 250 µM; Phi29 DNA polymerase in the range of 0.1 unit/ul to 5 unit/ul; and incubated in suitable buffer and salts such as Tris buffer, pH 7-8, and magnesium salt in the range of 0.5-10 mM.

In this example, the above reaction mixture is incubated at 30° C. for 1-18 hours, preferably 4-12 hours. The enzyme is then inactivated by incubating at 65° C. for additional 15 minutes. The amplified products, with base modified nucleotides incorporated and thus more relaxed secondary structure, are then subjected to cycle sequencing as described above.

Exonuclease resistant random hexamers can be purchased from Fermnetas (R106), or synthesized as phosphothiated oligos by standard methods. Phi29 DNA polymerase can be obtained from New England Biolab (M0296) or Fermentas. The enzyme can also be substituted with other phage DNA polymerase, such as T5 or RB69 polymerase. Recombinant versions of these enzymes can be prepared by standard cloning and protein purification methods.

In these methods, the promoting nucleotides can be incorporated into templates through initial rolling circle amplification, and the modified templates can then be sequenced with standard reagents. Incorporating promoting nucleotides through RCA, and then subjecting the RCA product to cycle sequencing, is suitable for amplification and sequencing of circular templates that contains GC rich or other repetitive sequence, as well as hairpin or other secondary structures.

The following examples are provided to describe the invention in further details. These examples are intended to illustrate specific applications of the invention and should in no way be construed as limiting the invention.

EXAMPLES

Example 1

Direct Cycle Sequencing of a DNA Template with GC-Rich Hairpin of 33 bps

Materials and Methods. Direct cycle sequencing involves amplification/strand extension with a single primer and both dNTPs for strand extension and ddNTPs for strand termination. The BigDye Terminator Cycle Sequencing Sequencing Kit (Applied BioSciences Inc./Life Technologies) was used according to manufacturer's instructions. BigDye dNTP mix substitutes dITP for dGTP to minimize band compressions (inadequate separation of the bands on a gel sequencing electrophoretogram). Promoting nucleotides were added at final concentrations of 20 µM dITP, 6.7 µM 5-propynyl-2'-dCTP, and 4 µM 8-oxo-dGTP. 2 µl of 2.5 µM sequencing primer, 4 µl BigDye mix containing dNTP mix, fluorescent-labeled ddNTPs, AmpliTaq DNA polymerase, and thermostable pyrophosphatase (Applied Bioscience Inc.) was prepared. 200 ng of DNA in 4 µl of this mixture was used as the template.

Strand extension was performed by sequential steps of annealing the primer to the template, replicate strand extension, and termination of replication over 25 cycles (96° C. for 12 seconds, 50° C. for 6 seconds and 60° C. for 3 minutes). Upon completion of the cycle sequencing reaction, excess labeled ddNTP was removed by ethanol precipitation. The labeled PCR products were resuspended in loading buffer (containing deionized formamide and EDTA), denatured, and separated by capillary electrophoresis on an ABI Prism 3710 sequencer (Applied Bioscience Inc.). KB Basecaller software (Invitrogen) was applied to convert the chromatogram into sequence files.

Figure 2A:
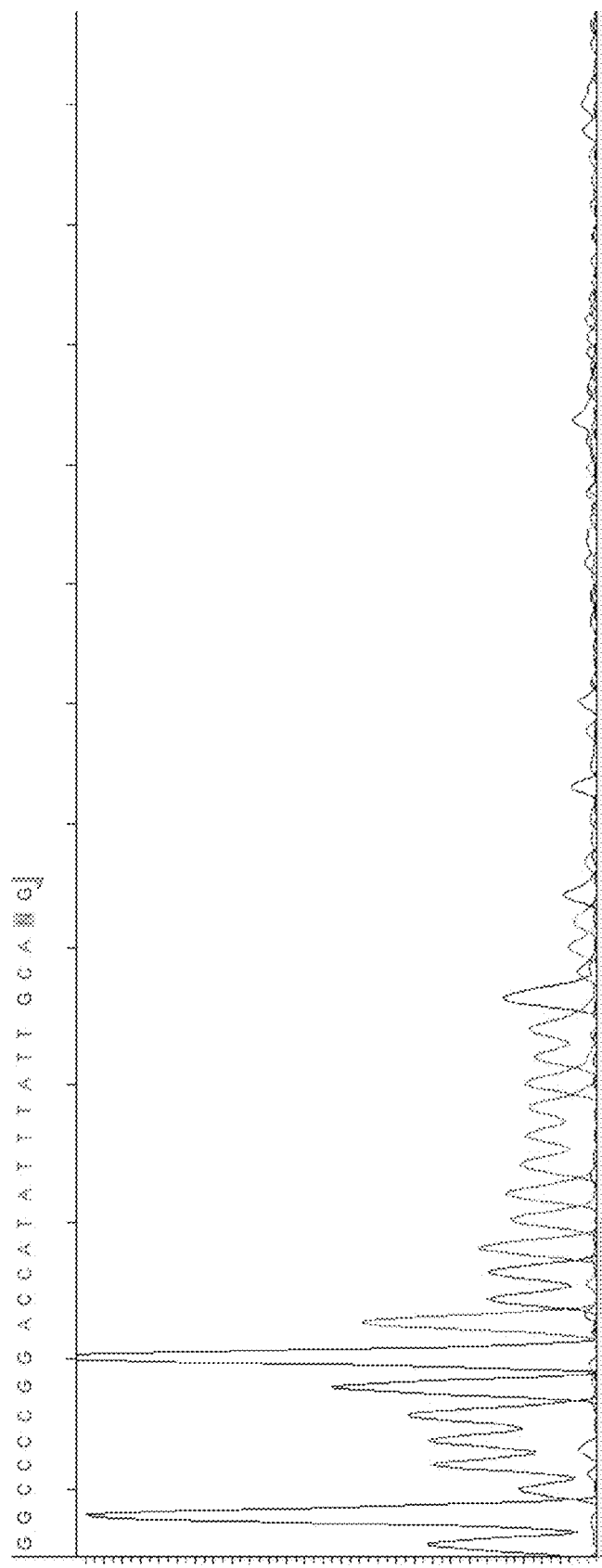
FIGS. 2A-2B. Sequence chromatogram of the template of FIG. 1 sequenced directly with (A) a standard cycle sequencing reagent (BigDye from ABI) (chromatogram nucleotide sequence, SEQ ID NO: 2) or with (B) a standard sequencing reagent (BigDye) with addition of dITP, 5-propynyl-dCTP, and 8-oxo-dGTP (chromatogram nucleotide sequence, SEQ ID NO: 3).
Figure 2B:
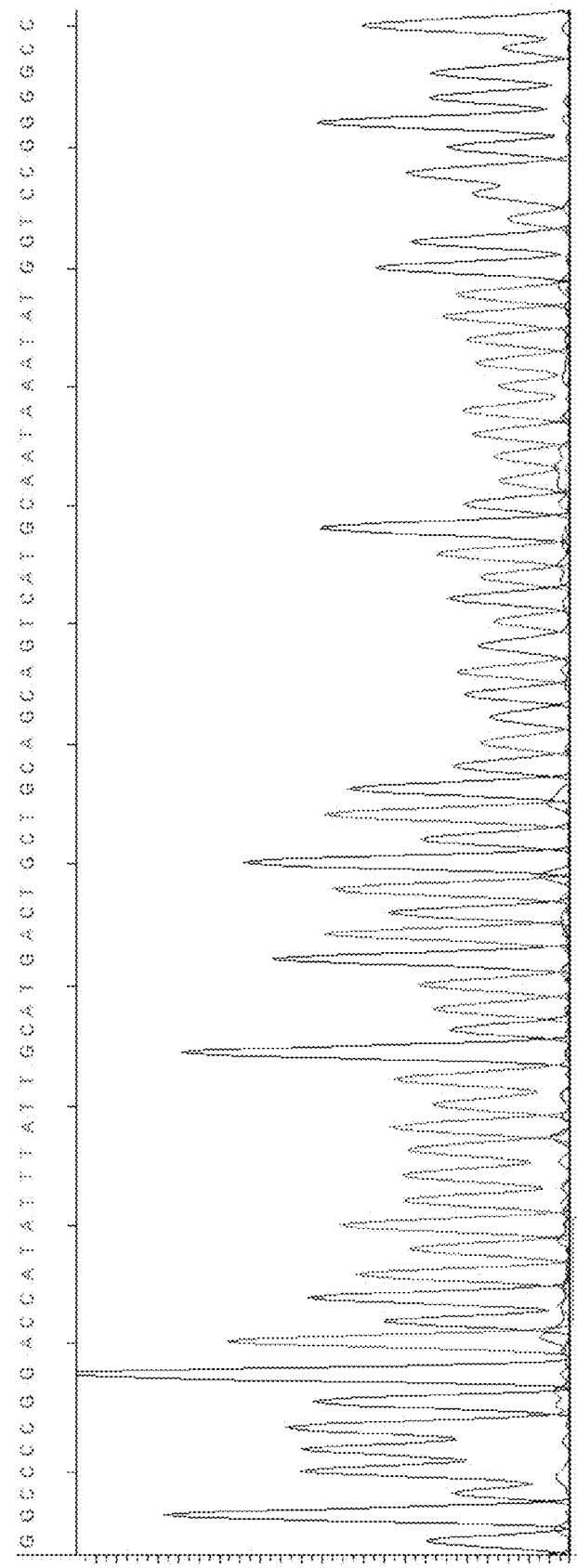

Results. As shown in FIG. 1, a template with 33 base pair (bp) inverted repeats separated by 4 nucleotides forms a hairpin, locked with 9 strong-binding GC base pairs at the end of the stem. This type of GC-rich hairpin is typically difficult to amplify and sequence by standard means. When the template was incubated with BigDye cycle sequencing reaction mixtures, the chromatogram stalls about ⅓ to ½ through the length of the hairpin (FIG. 2A). However, when the same template is incubated with a combination of promoting nucleotides dITP, 5-propynyl-dCTP, and 8-oxo-dGTP in addition to BigDye cycle sequencing mix, the chromatogram ran through the entire hairpin and continued (FIG. 2B). Table 1 shows the continuous read length increases from 220 bp with regular BigDye to 896 bp when BigDye is enhanced by addition of the promoting nucleotides. Table 1 also shows that the promoting nucleotides are even more effective than dGC dye, an ABI product specifically designed for difficult templates.

TABLE 1

Read lengths for hairpin DNA sequence using standard sequencing reagents, and with standard reagents plus promoting nucleotides dITP, 5-propynyl-dCTP, and 8-oxo-dGTP.

| | Trace score | Continuous read length |
|---|---|---|
| BigDye | 37 | 221 |
| dGC dye | 31 | 538 |
| BigDye with promoting nucleotides | 38 | 809 |

Example 2

Rolling Circle Amplification and Cycle Sequencing of a DNA Template with a GC-Rich Hairpin of 33 bps Materials and Methods. 1 µl template containing 1-5 ng of DNA was mixed with 2 µl of sample buffer containing 50 µM of random hexamers in Tris-MgCl$_2$ buffer, denatured at 95° C. for 3 minutes, and cooled on ice. The DNA template was amplified by F29 DNA polymerase in the presence of regular dNTPs (the dNTP mix containing 0.5 mM each of dATP, dCTP, dGTP and dTTP) or dNTPs with promoting nucleotides (the dNTP mix containing 0.5 mM dATP, 0.5 mM dTTP, 0.25 mM dITP, 0.125 mM 8-oxo-dGTP, 0.125 mM dGTP, 0.4 mM dCTP, and 0.1 mM 5-propynyl-2'-dCTP). 2 µl of reaction mixture (containing 0.5 mM of either dNTP mix and 5 units of F29 DNA polymerase in the same buffer) was added to the template, and incubated at 30° C. for 3-12 hours. At the end of incubation, the enzyme was inactivated by incubating the mixture at 65° C. for 15 minutes. The amplified product was sequenced with BigDye Terminator v.3.1 cycle sequencing kit (ABI) according to the manufacturer's instructions.

Figure 3A:
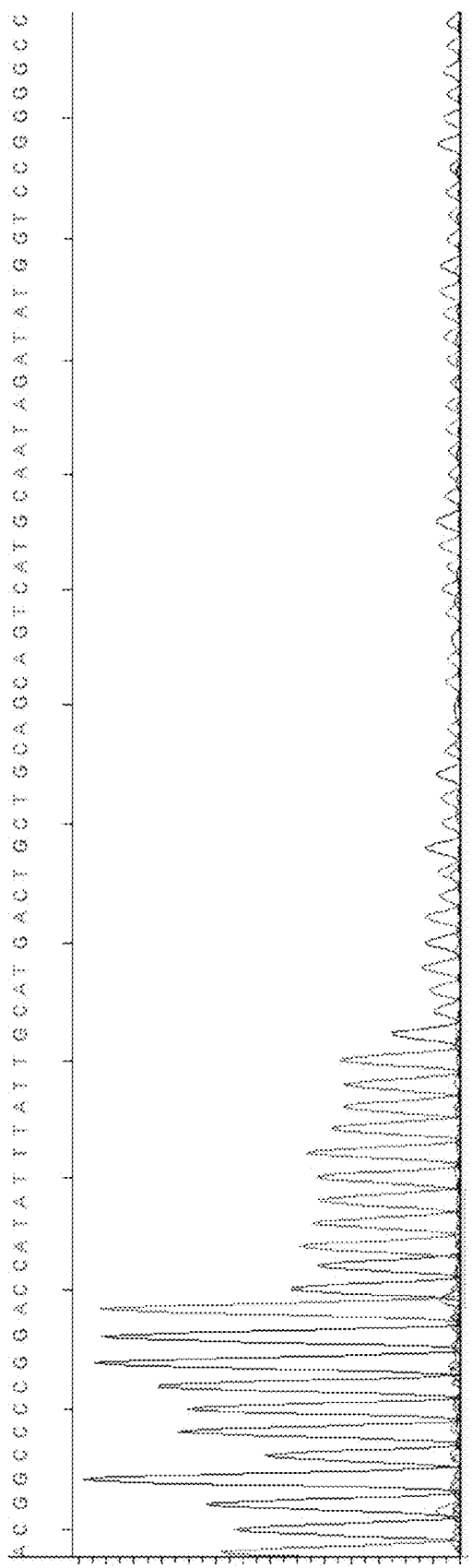
FIGS. 3A-3F. Sequence chromatogram of the template of FIG. 1, sequenced following rolling circle amplification (RCA) with (A) standard nucleotides (chromatogram nucleotide sequence, SEQ ID NO: 4) or (B) 8-oxo-dGTP (chromatogram nucleotide sequence, SEQ ID NO: 5); (C) 5-propynyl-dCTP (chromatogram nucleotide sequence, SEQ ID NO: 6); (D) dITP and 5-propynyl-dCTP (chromatogram nucleotide sequence, SEQ ID NO: 7); (E) dITP and 8-oxo-dGTP (chromatogram nucleotide sequence, SEQ ID NO: 8) or (F) dITP, 5-propynyl-dCTP, and 8-oxo-dGTP (chromatogram nucleotide sequence, SEQ ID NO: 9).
Figure 3B:
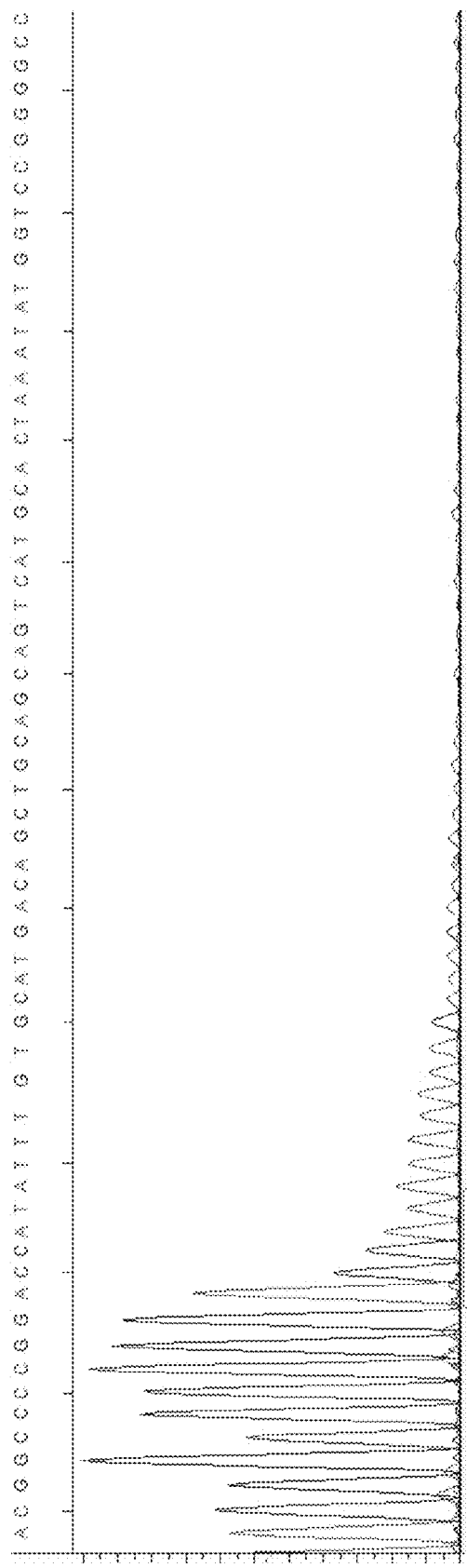
Figure 3C:
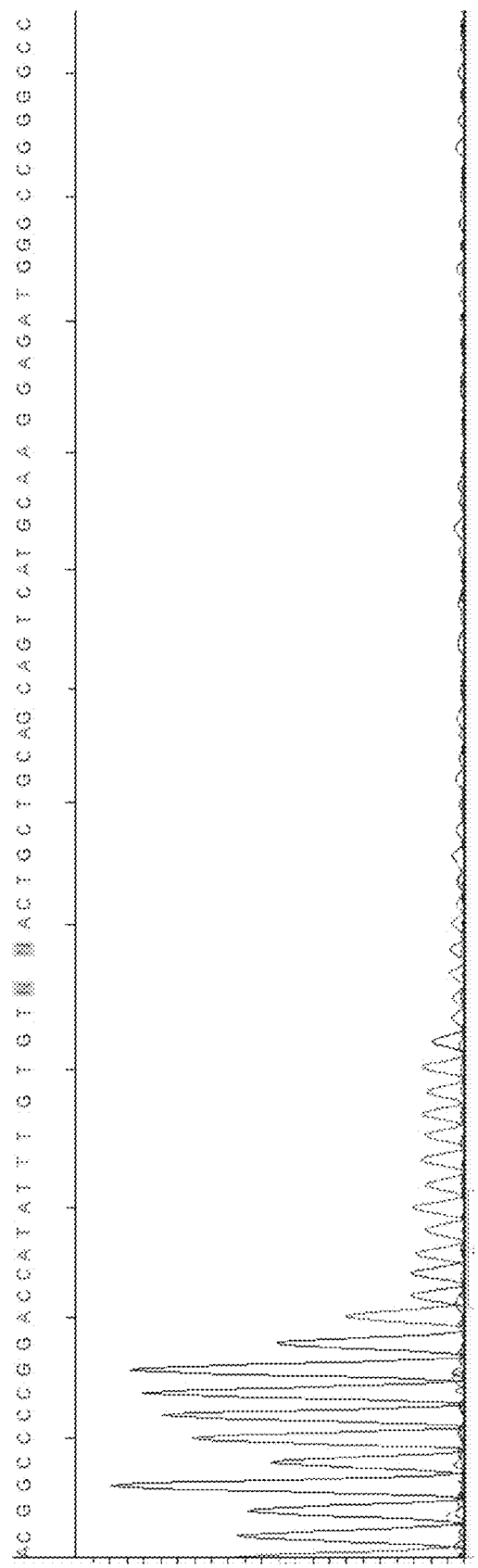
Figure 3D:
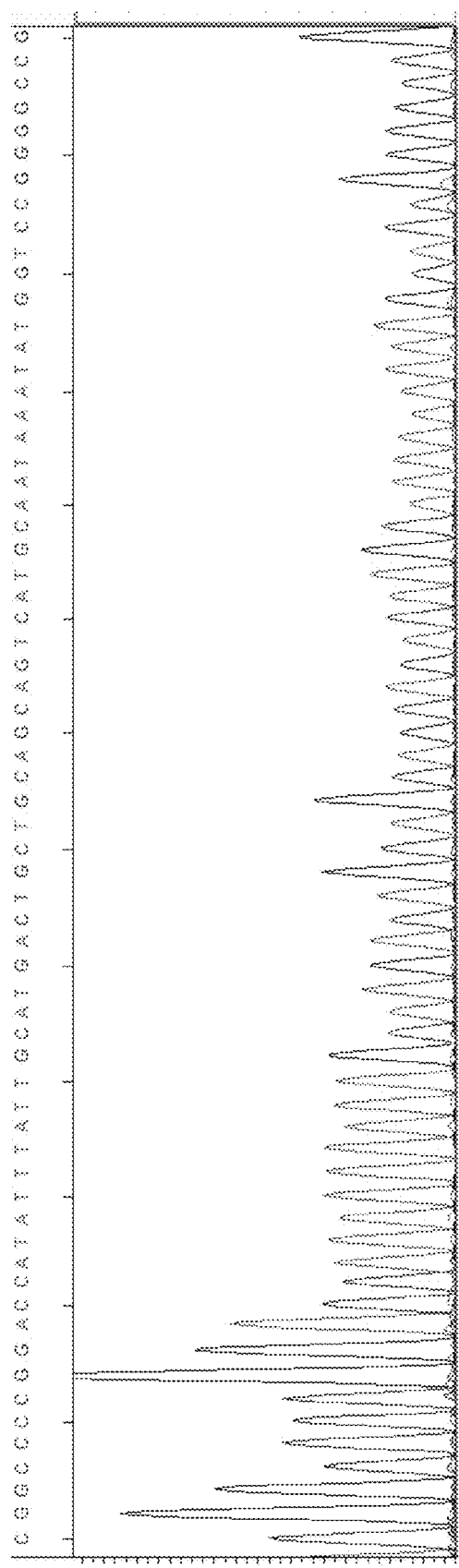
Figure 3E:
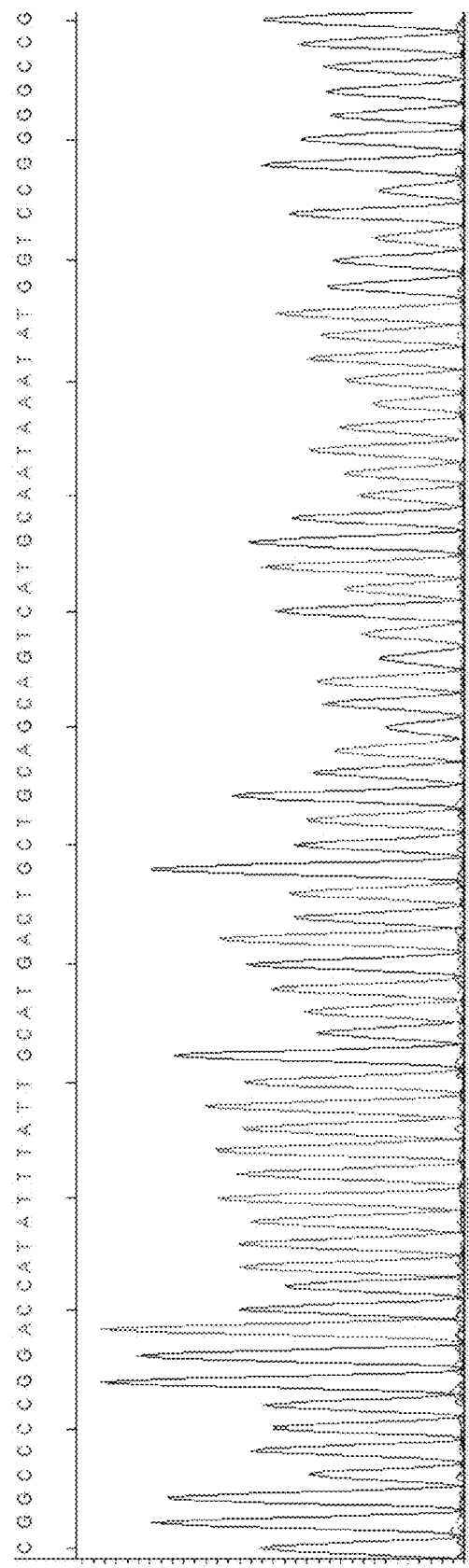
Figure 3F:
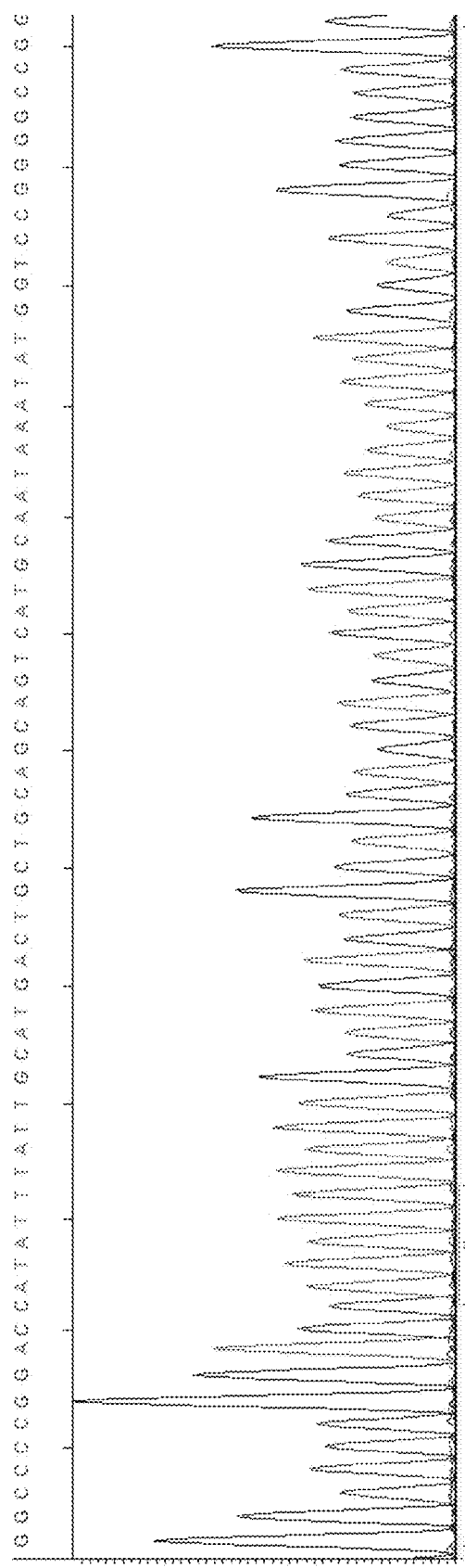

Results. The promoting nucleotides enable amplification of the GC-rich hairpin template of Example 1 by a mesophilic DNA polymerase, Phage 29 (Phi29) polymerase. As shown in FIGS. 3E and 3F, Phi29 DNA polymerase was best able to amplify the template containing hairpin secondary structure when incubated with dITP and 8-oxo-dGTP (FIG. 3E) or dITP, 5-propynyl-dCTP, and 8-oxo-dGTP (FIG. 3F). In contrast, in the absence of dITP, 8-oxo-dGTP, and 5-propynyl-dCTP, or dITP and 5-propynyl-dCTP, either Phage 29 failed to amplify the hairpin-containing template, or the amplified product failed to be cycle sequenced (FIGS. 3A-3C).

Example 3

RCA Amplification and Cycle Sequencing of GT Rich and Poly C Templates

Materials and Methods. RCA followed by cycle sequencing was performed as for Example 2.

Figure 4A:
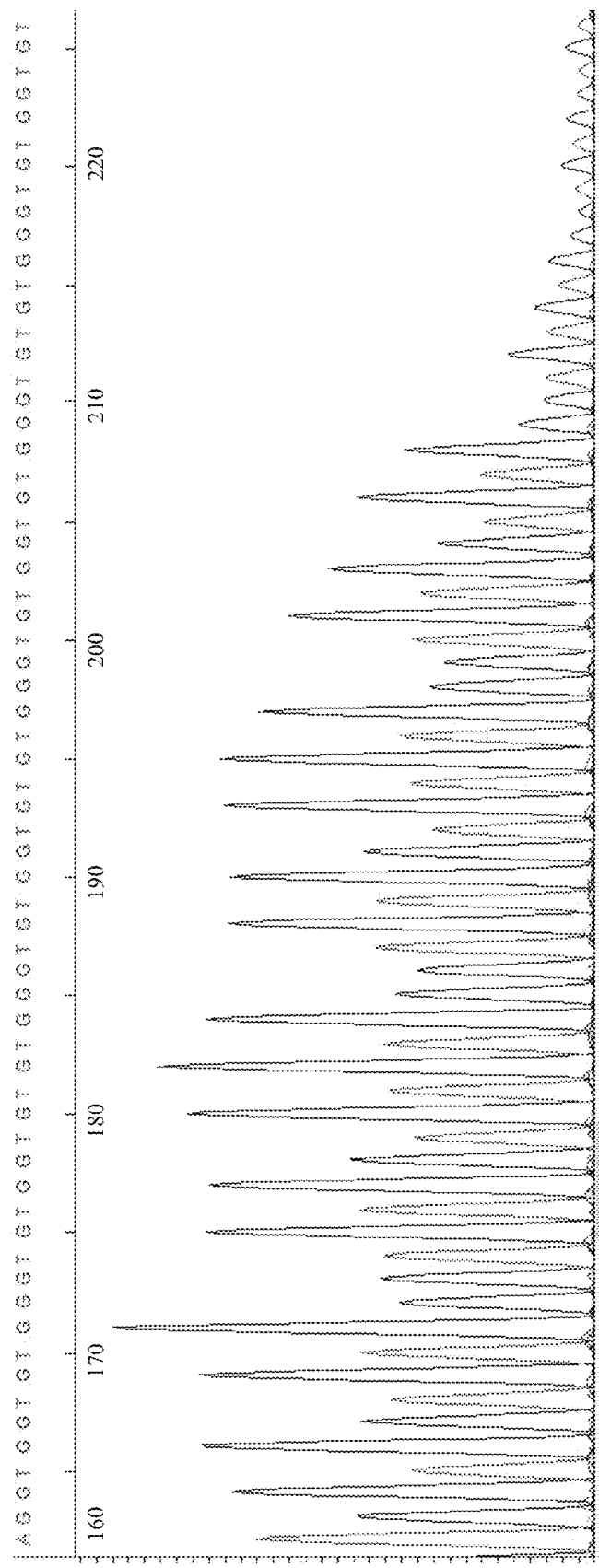
FIGS. 4A-4B. Sequence chromatogram of a DNA template with a 104 bp stretch of GT repeats, followed by a 19 bp stretch of poly C repeats, sequenced after RCA amplification with standard nucleotides and (A) dITP (chromatogram nucleotide sequence, SEQ ID NO: 10) or (B) dITP, 5-propynyl-dCTP, and 8-oxo-dGTP (chromatogram nucleotide sequence, SEQ ID NO: 11).
Figure 4A:
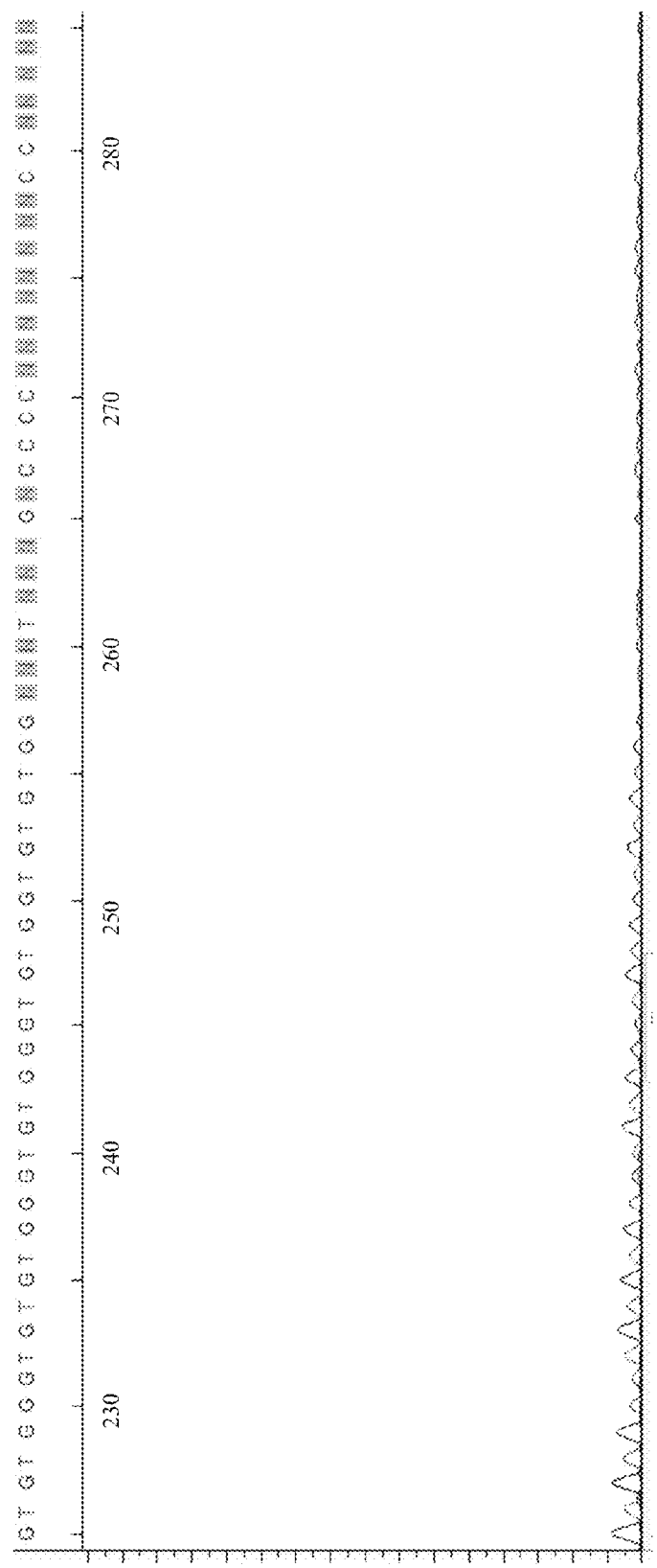
Figure 4B:
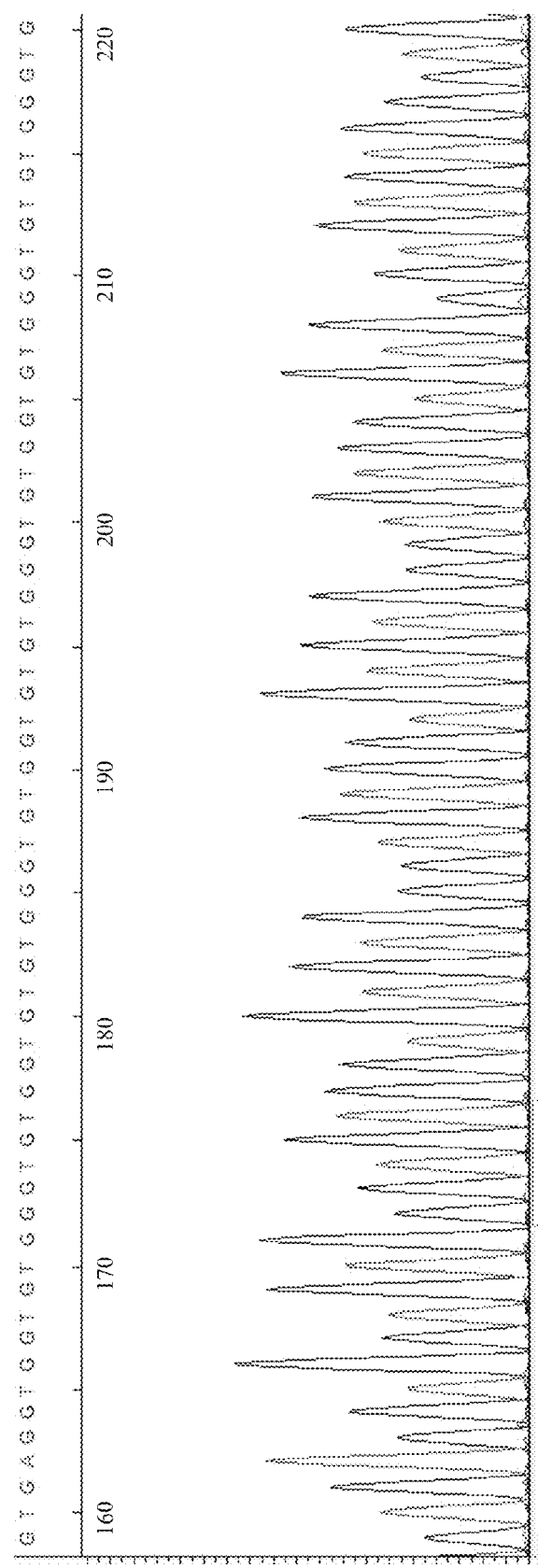
Figure 4B:
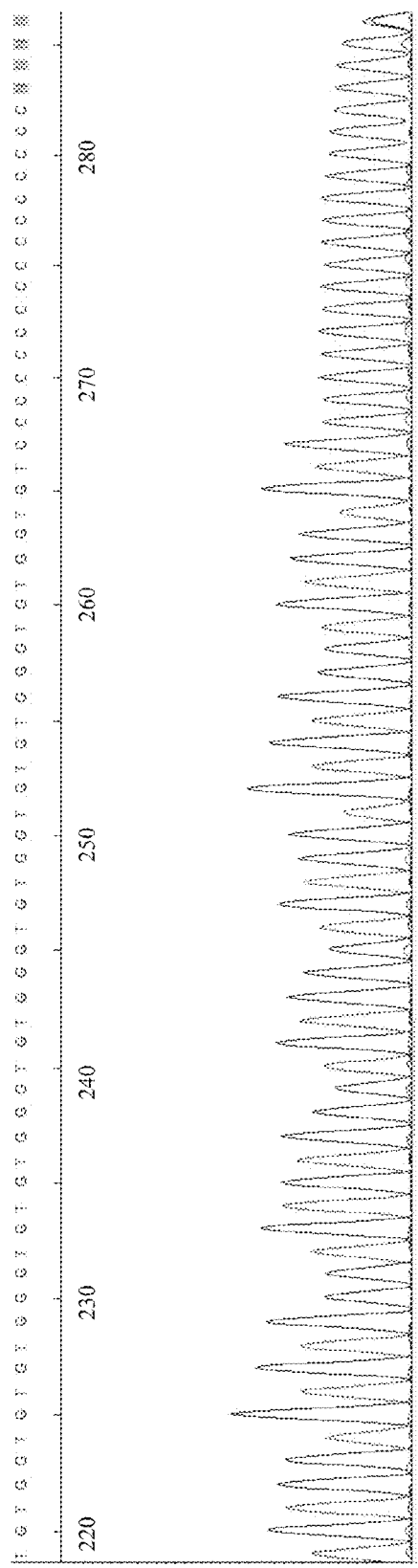
Figure 5B:
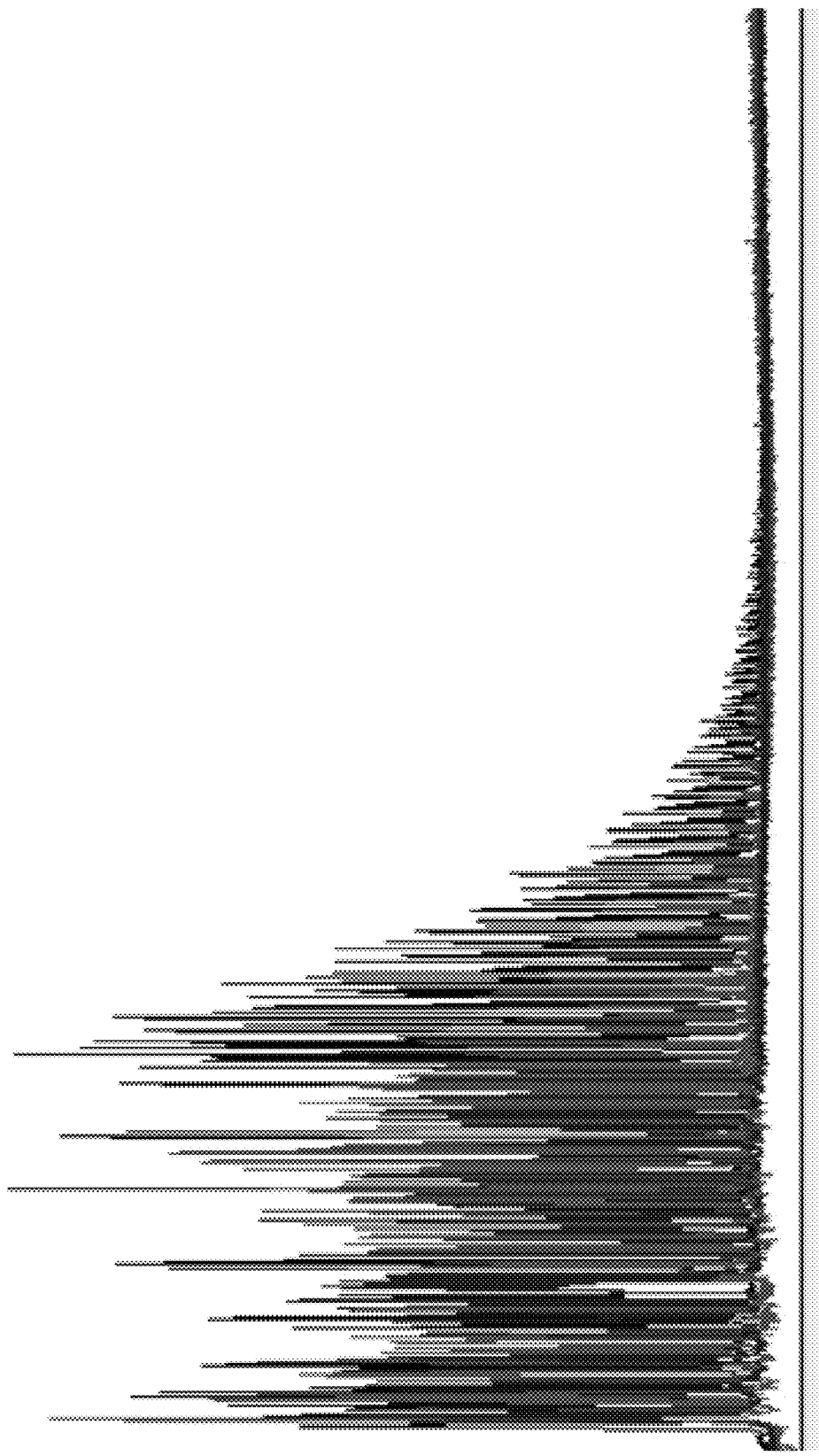
Figure 5C:
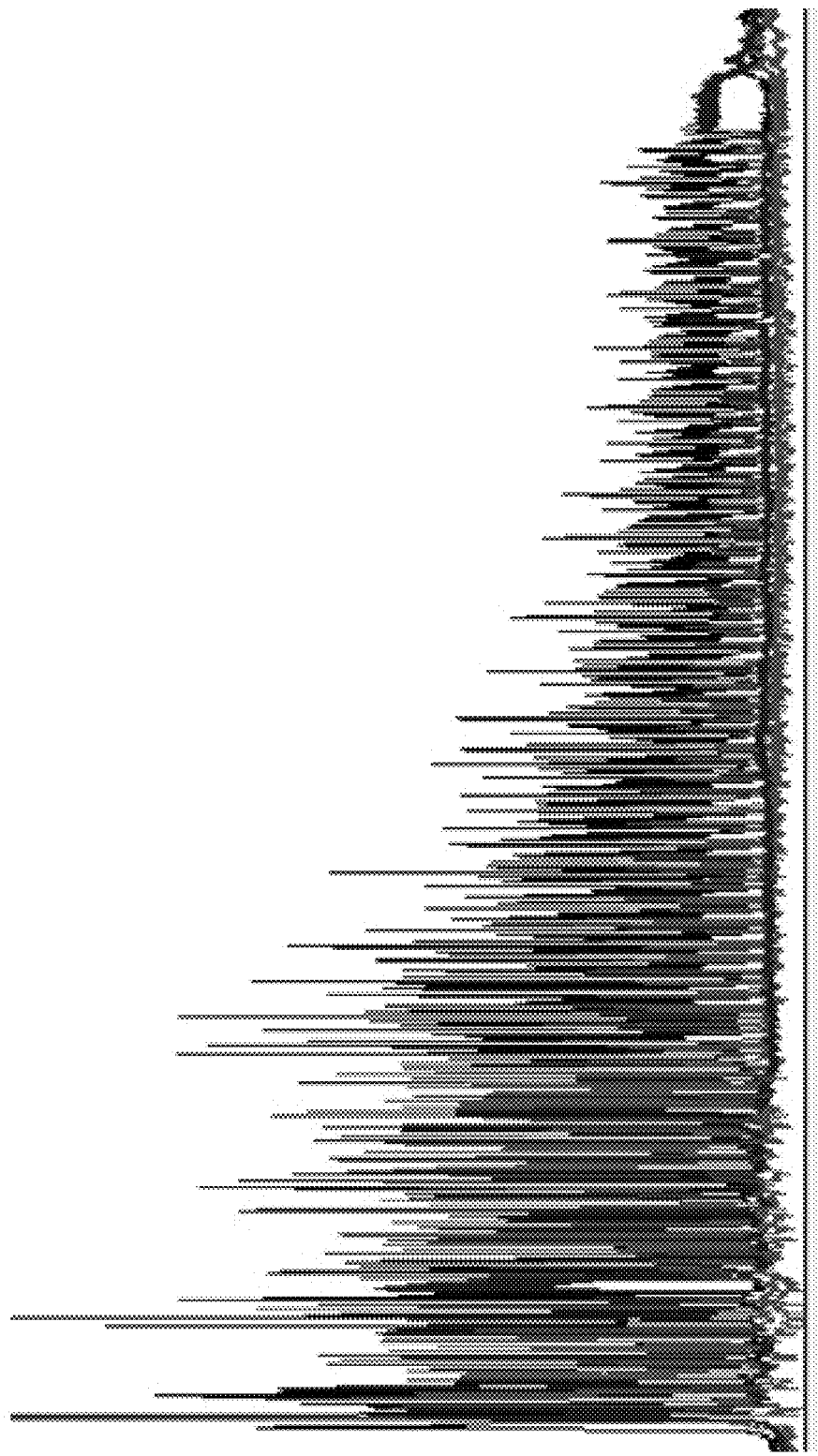
Figure 5D:
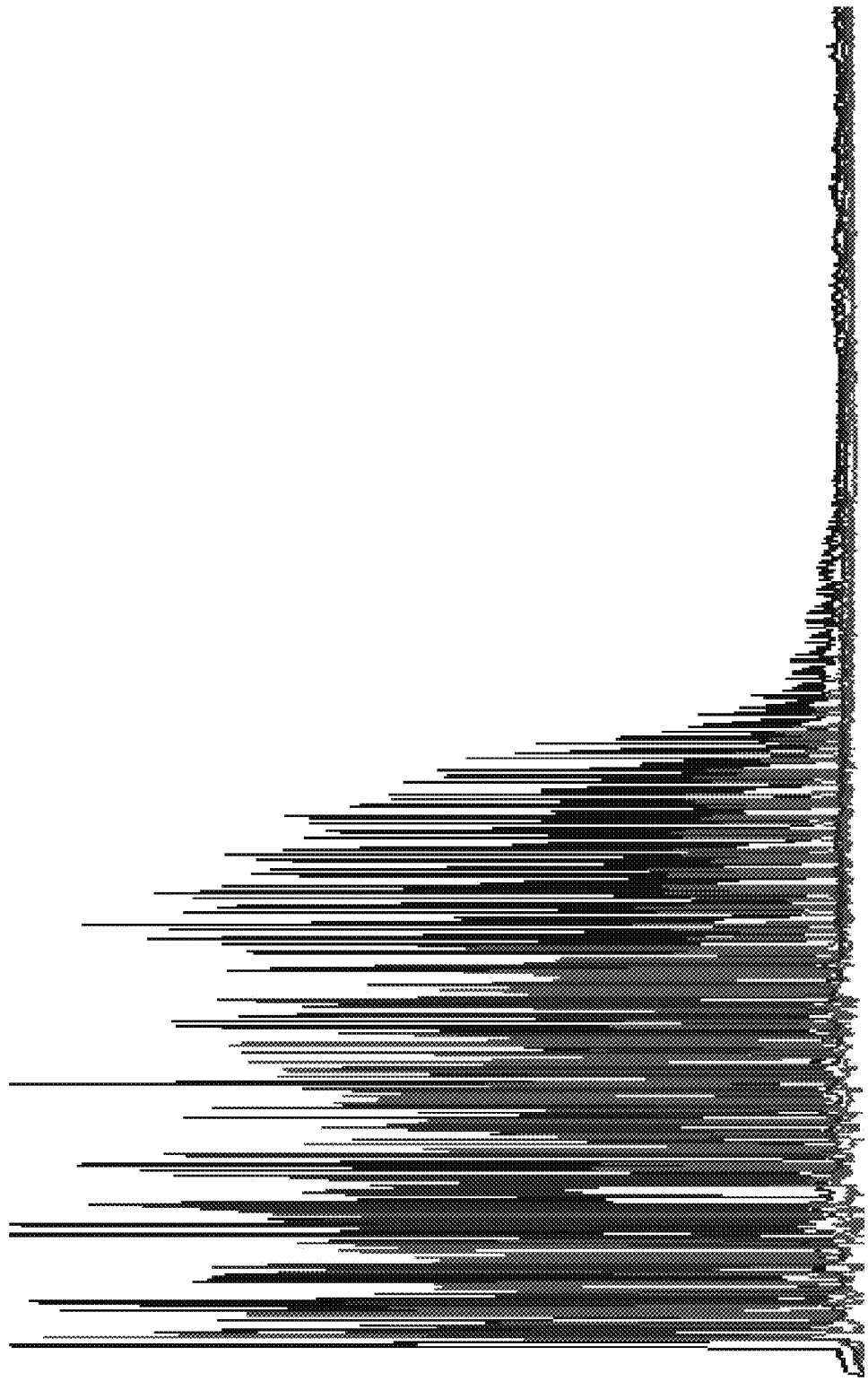
Figure 5E:
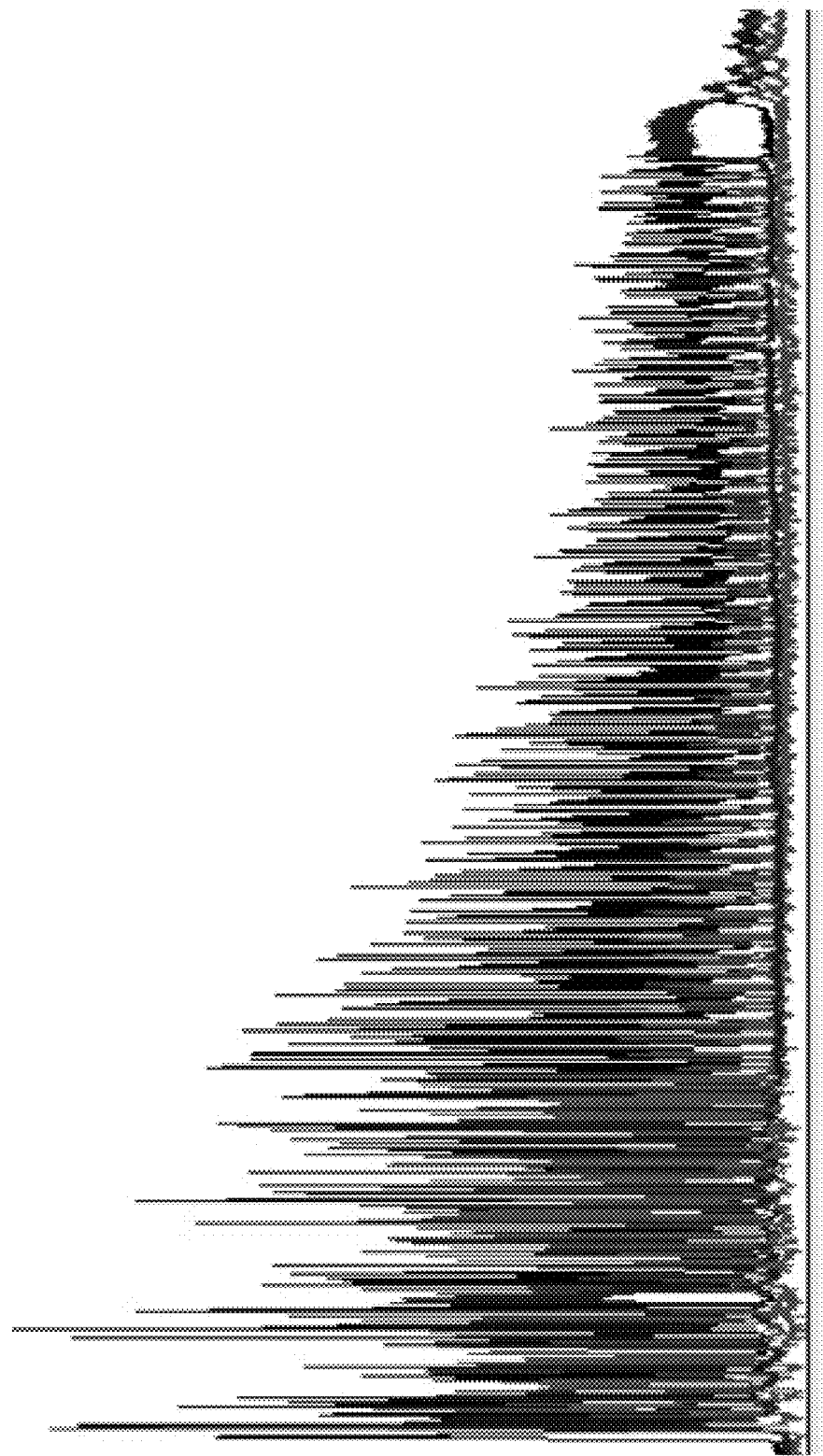

Results. The promoting nucleotides made it possible to amplify and sequence templates with long stretches of repetitive sequence. A template with 104 bp of GT repeats, followed by 19 bp of poly C repeats was successfully amplified in presence of the promoting nucleotides using Phage 29 DNA polymerase (FIG. 4B) but not in the absence of a combination of the three promoting nucleotides (FIG. 4A). Similarly, a template with 334 bp of GT repeats, followed by 23 bp of poly C repeats, was successfully amplified in presence of the combinations of dITP and 5-propynyl-dCTP (FIG. 5C) or dITP, 5-propynyl-dCTP, and 8-oxo-dGTP (FIG. 5E) using Phage 29 DNA polymerase, but not with dITP alone (FIG. 5A), 5-propynyl-dCTP alone (FIG. 5B), or dITP and 8-oxo-dGTP (FIG. 5D).

Thus, combinations of two to three of the promoting nucleotides dITP, 5-propynyl-dCTP, and 8-oxo-dGTP provide improved amplification and sequencing of DNA sequences that are not amenable to standard amplification and sequencing techniques.

What is claimed is:

1. A method for amplifying a DNA template, comprising:
   a. providing a DNA template and an exonuclease-resistant random hexamer primer;
   b. denaturing said DNA template;
   c. annealing said DNA template with said primer; and
   d. incubating said template and said primer with a nucleotide composition comprising at least two of: 2'-deoxyinosine-5' triphosphate, 5-propynyl-2'-deoxycytidine-5'-triphosphate, and 8-oxo-2'-deoxyguanosine-5'-triphosphate, for a time sufficient for said template to be amplified.

2. The method of claim 1, wherein the DNA template is a circular DNA template.

3. The method of claim 2, wherein said circular DNA template comprises at least one of the following: a GC rich or GT rich sequence, a homopolymer repetitive sequence; or a hairpin secondary structure.

4. The method of claim 1, wherein said circular DNA template is provided in step (a) in an amount of 1 pg to 500 ng.

5. The method of claim 1, wherein said template and said primer are incubated in step (d) at 28-32° C. for 2-18 hours.

6. The method of claim 1 wherein in step (d) said template and said primer are incubated with a composition comprising:
   a mixture of nucleotides dATP, dCTP, dGTP and dTTP,
   DNA polymerase with strand displacement activity,
   a buffer,
   a magnesium salt, and
   one or more ammonia sulfate salts,
   for a time sufficient for said template to be amplified.

7. The method of claim 1, wherein the nucleotide composition of step (d) comprises all three of 2'-deoxyinosine-5' triphosphate, 5-propynyl-2'-deoxycytidine-5'-triphosphate, and 8-oxo-2'-deoxyguanosine-5'-triphosphate.

* * * * *